(12) United States Patent
Salsman (10) Patent No.: US 8,717,556 B2
(45) Date of Patent: *May 6, 2014

(54) MICROFLUIDIC SYSTEMS WITH CHEMICAL PUMPS

(75) Inventor: Kenneth Edward Salsman, Pleasanton, CA (US)

(73) Assignee: Aptina Imaging Corporation, George Town (KY)

( * ) Notice: Subject to any disclaimer, the term of this patent is extended or adjusted under 35 U.S.C. 154(b) by 0 days.

This patent is subject to a terminal disclaimer.

(21) Appl. No.: 13/469,040

(22) Filed: May 10, 2012

(65) Prior Publication Data

US 2013/0027695 A1    Jan. 31, 2013

Related U.S. Application Data

(60) Provisional application No. 61/512,299, filed on Jul. 27, 2011.

(51) Int. Cl.
*G01N 21/01* (2006.01)
*C12Q 1/02* (2006.01)
*H01L 27/146* (2006.01)

(52) U.S. Cl.
USPC .......... 356/246; 356/445; 435/29; 435/287.2; 438/79

(58) Field of Classification Search
USPC ........ 356/246, 445, 72–73, 326, 440; 435/29, 435/287.2, 288.7; 348/79, 249, 222.1
See application file for complete search history.

(56) References Cited

U.S. PATENT DOCUMENTS 7,435,578 B2 * 10/2008 Wikswo et al. ............ 435/288.3
7,466,409 B2 * 12/2008 Scherer et al. ............... 356/326
7,524,459 B2 * 4/2009 Adams et al. ............. 422/82.05
7,751,048 B2    7/2010 Yang et al.
8,465,698 B2 * 6/2013 Yamakawa et al. ........ 422/82.05
2003/0235924 A1 * 12/2003 Adams et al. ................. 436/172

(Continued)

FOREIGN PATENT DOCUMENTS

| EP | 1442787 | 8/2004 |
| EP | 2258951 | 12/2010 |
| WO | 2009111573 | 9/2009 |
| WO | 2011073410 | 6/2011 |

OTHER PUBLICATIONS

Good et al., "An effervescent reaction micropump for portable microfluidic systems", Lab on a Chip, Royal Society of Chemistry, vol. 6, No. 5, Jan. 1, 2006 (pp. 659-666).

*Primary Examiner* — Sang Nguyen
(74) *Attorney, Agent, or Firm* — Treyz Law Group; Louis R. Levenson; Jennifer Luh (57) ABSTRACT

A microfluidic system may include an image sensor integrated circuit containing image sensor pixels. A channel containing a fluid with particles such as cells may be formed on top of the image sensor. Flow control components may be mounted to the image sensor integrated circuit for controlling the flow of fluids through the channel. The flow control components may include a chemically powered pump. The chemical pump may include one or more chambers and a valve between the chambers. The valve may be operable to allow chemical reactants stored in the chambers to be mixed to produce gasses for generating pressure in the channel. The pressure in the channel may be used to control the flow of the fluid. As the fluid and particles flow through the channel, the image sensor pixels may be used to capture images of the particles.

14 Claims, 11 Drawing Sheets

(56) References Cited

U.S. PATENT DOCUMENTS

| | | |
|---|---|---|
| 2004/0115731 A1* | 6/2004 | Hansen et al. ............... 435/7.1 |
| 2010/0186524 A1* | 7/2010 | Ariessohn et al. ......... 73/863.22 |
| 2011/0181884 A1* | 7/2011 | Cui et al. ..................... 356/436 |
| 2011/0311394 A1 | 12/2011 | Worsman et al. |
| 2012/0044341 A1* | 2/2012 | Stith et al. ...................... 348/79 |
| 2012/0045786 A1* | 2/2012 | Stith ............................... 435/29 |

* cited by examiner

MICROFLUIDIC SYSTEMS WITH CHEMICAL PUMPS

This application claims the benefit of provisional patent application No. 61/512,299, filed Jul. 27, 2011, which is hereby incorporated by reference herein in their entireties.

BACKGROUND

This relates generally to microfluidic systems and, more particularly, to microfluidic systems with pumps for moving fluids within the microfluidic systems.

Conventional microfluidic systems are provided with plastic molded or laminated structures to store, move, and react a combination of reagents, dyes, and samples for a variety of analytical functions. In a typical microfluidic system, separate pumping and flow control devices are required to move the fluids and/or reactants from one position within the microfluidic system to another. These separate pumping and flow control devices often include pumping and valve structures that are significantly larger than the microfluidic structures. For example, typical systems include relatively small sample handling structures but utilize desktop plumbing systems that contain numerous pumps and valves to provide flow drive and control across the microfluidic system. This type of system can require training and operational expertise to use, as well as adding significant cost to the system, making the system non-portable, and requiring significant power to operate.

It would therefore be desirable to be able to provide improved microfluidic systems.

DETAILED DESCRIPTION

Systems such as microfluidic systems may be provided with internal flow control structures for moving fluids, samples, particles, reactants or reagents from one part of the system to another. A microfluidic system may be used to image and otherwise evaluate cells and other samples such as biological specimens. The internal flow control structures may include one or more chemically powered pumps.

Figure 1:
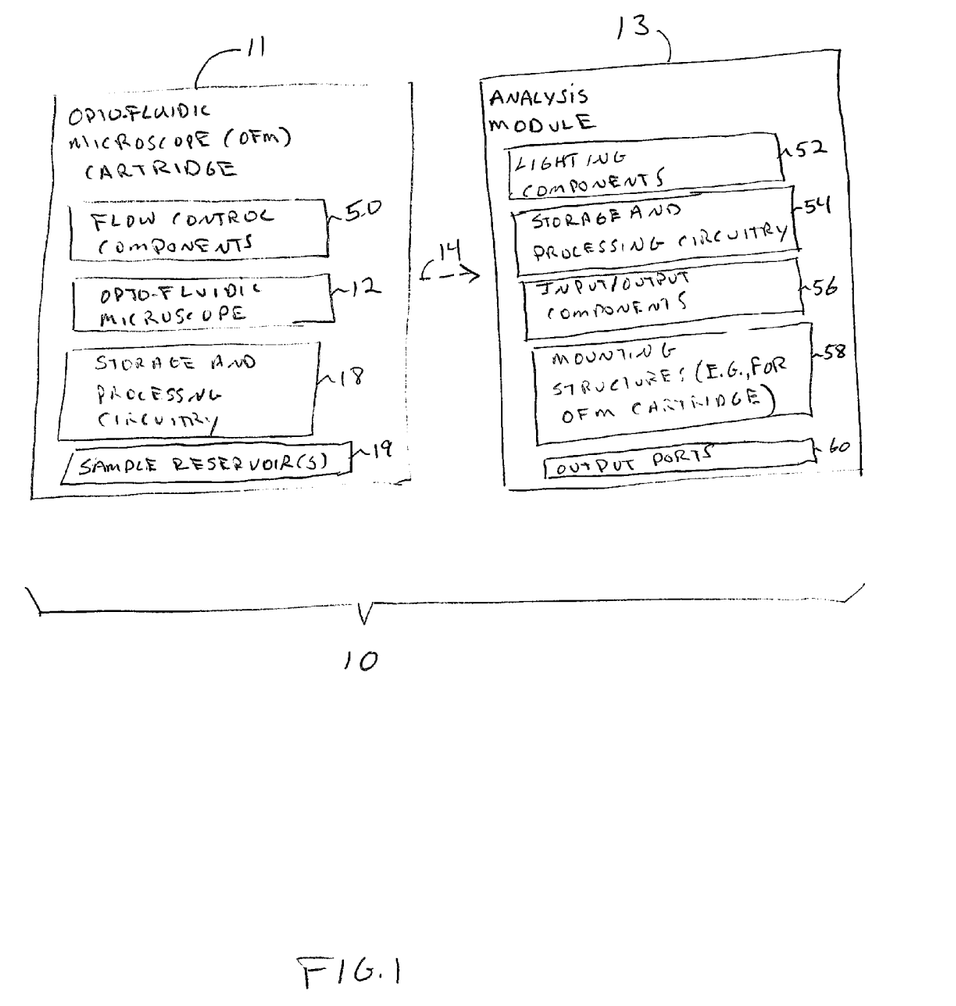
FIG. 1 is a diagram of an illustrative system for imaging and processing cells and other biological specimens in accordance with an embodiment of the present invention.

A system of the type that may be used to image and otherwise evaluate cells and other samples such as biological specimens is shown in FIG. 1. As shown in FIG. 1, system 10 may include optofluidic microscope cartridge 11 and analysis module 13. Analysis module 13 may be formed in a common package with optofluidic microscope cartridge 11 or may be a separate module configured to receive optofluidic microscope cartridge 11 (as indicated by arrow 14). Analysis module 13 may, for example, be used to analyze samples in multiple, disposable optofluidic microscope cartridges such as cartridge 11. Optofluidic microscope cartridge 11 and analysis module 13 may each have a relatively small size. For example, optofluidic microscope cartridge 11 may have a maximum lateral width of less than one inch, less than half of one inch, less than one quarter of one inch, less than four inches, or less than 10 inches. Analysis module 13 may have a maximum lateral length of less than three inches, less than two inches, less than one inch, less than four inches, or less than 10 inches.

Optofluidic microscope cartridge 11 may be configured to receive samples such as biological samples in a fluid. Optofluidic microscope cartridge 11 may include an optofluidic microscope (OFM) 12 for imaging and evaluating the samples. Optofluidic microscope cartridge 11 may include control circuitry such as storage and processing circuitry 18 for performing operations such as operating optofluidic microscope 12. Circuitry 18 may include circuitry formed on a common integrated circuit die with optofluidic microscope 12 or may include circuitry such as microprocessors, integrated circuits or other circuits on a printed circuit board that is separate from or coupled to optofluidic microscope 12.

Optofluidic microscope cartridge 11 may include components such as flow control components 50 for controlling the flow of fluids within fluid channels in OFM 12. Flow control components 50 may, for example, include one or more chemically powered pumps for providing pressure within OFM 12 for moving and directing fluids through OFM 12. Flow control components 50 may include one or more chambers for storing chemicals and a valve operable to allow mixing of those chemicals. Pressure may be generated within OFM 12 by gasses that result from the mixing of the chemicals when the valve is operated. If desired, flow control components 50 may include additional components such as pressure stabilization chambers and feedback mechanisms for maintaining a constant pressure within OFM 12 during sample analysis operations. Flow control components 50 may include gating structures within fluid flow channels or other flow control components within fluid flow channels in OFM 12. OFM cartridge 11 may include one or more sample reservoirs 19 for temporarily storing injected samples. Flow control components such as chemical pumps may be coupled to sample reservoirs 19 and/or directly to fluid flow channels in OFM 12. In this way, pressure generated by chemical pumps may be used to move samples or reactants within OFM 12 and/or operate flow control structures such as gates within channels within OFM 12.

OFM cartridge 11 may further include temperature control elements such as one or more resistive elements that increase in temperature when a current is applied or other temperature control elements for cooling some or all of OFM 12 during sample analysis operations. Circuitry 18 of OFM cartridge 11 may be configured to operate temperature control components for temperature control of OFM 12 during sample imaging and analysis operations.

Analysis module 13 may include control circuitry such as storage and processing circuitry 54. Storage and processing circuitry 54 of analysis module 13 may include circuitry that is separate from storage and processing circuitry 18 of OFM cartridge 11 or may have portions that are formed in common with storage and processing circuitry 18 of OFM cartridge 11. Storage and processing circuitry 54 may include volatile memory (e.g., static or dynamic random-access memory), non-volatile memory (e.g., flash memory), microprocessors, integrated circuits, printed circuit boards or other circuitry. Storage and processing circuitry 54 may be used for storing, processing, and analyzing image data captured using OFC cartridge 11, and/or for operating components such as lighting components 52 and input/output components 56.

Storage and processing circuitry 54 may include communications circuitry such as circuitry coupled to output ports 60. Storage and processing circuitry 54 and/or storage and processing circuitry 18 may include wireless communications circuitry to be used to convey data such as image data to external equipment such as a computer, a handheld electronic device, a cellular telephone, a network router, a network antenna, etc. For example, wireless communications circuitry associated with circuitry 18 or circuitry 54 may be configured to transmit or receive data at WiFi® frequencies (e.g., 2.4 GHz and 5 GHz), Bluetooth® frequencies (e.g., 2.4 GHz), cellular telephone frequencies (e.g., 850 MHz, 900 MHz, 1800 MHz, 1900 MHz, and 2100 MHz), or other frequencies.

Output ports 60 may include one or more universal serial bus (USB) ports, serial ports, audio ports, video ports, etc. coupled to storage and processing circuitry 54.

Data that may be transmitted using ports 60 or wireless communications circuitry associated with storage and processing circuitry 18 and/or 54 may include identifying data of a particular analysis module, identifying data of a sample, geographic location data identifying the location of the analysis module, analysis data resulting from analysis of a sample within an OFM cartridge 11 or imaging data obtained using OFM cartridge 11 (as examples).

System 10 may provide a user with the ability to interact with analysis module 13. User interactions may include inputting identifying information (e.g., information identifying a sample, a sample donor, a geographic location, etc.) and obtaining output information (e.g., reading the result of an analysis performed using the optofluidic microscope). To implement these interactions, electronic device 10 may have input/output components 56 such as keypads, virtual keypads, buttons, displays, or other suitable input-output components. Input/output components 56 may include circuitry coupled to one or more output ports such as output port 60 mounted in a housing structure.

If desired, portions of analysis module 13 such as a housing may include mounting structures 58 for coupling OFM cartridge 11 to analysis module 13. Mounting structures 58 may include engaging portions of a housing for coupling OFM cartridge 11 to analysis module 13.

Lighting components 52 may include one or more light sources such as light-emitting-diodes (LEDs) and one or more optical components such as lenses, mirrors, gratings, etc. If desired, lighting components 52 may be mounted within one of mounting structures 58. Lighting components 52 may be mounted adjacent to a transparent portion of a housing member so that light generated by lighting components 52 may be provided to OFM 12 of OFM cartridge 11.

Figure 2:
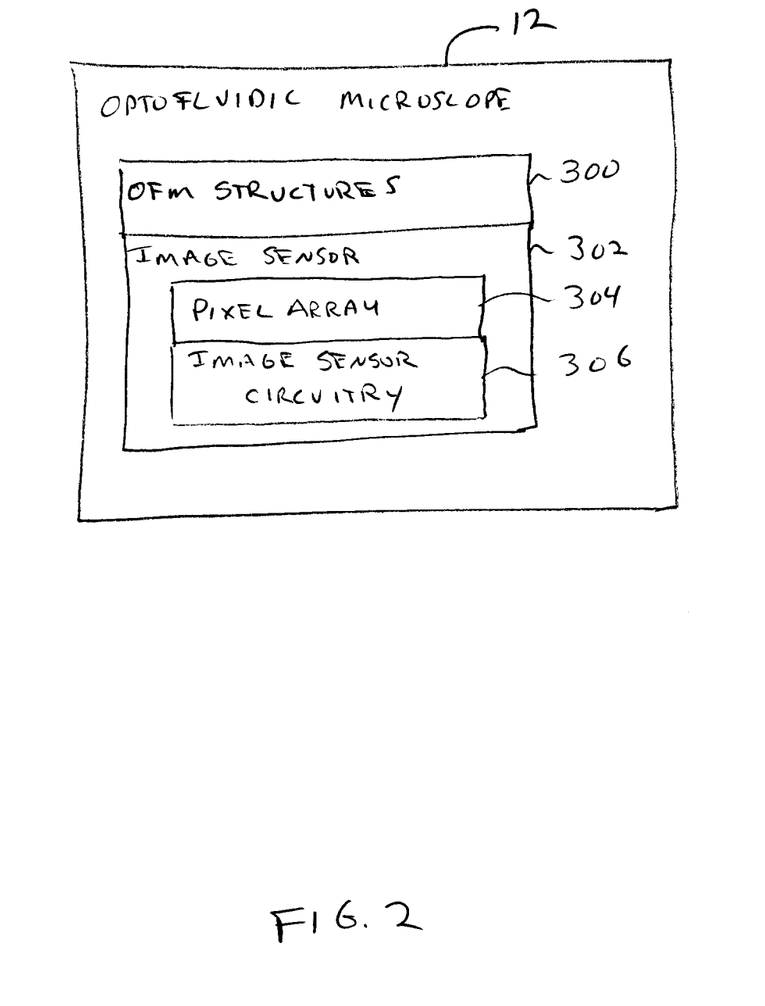
FIG. 2 is a diagram of an illustrative optofluidic microscope in accordance with an embodiment of the present invention.

An illustrative configuration that may be used for optofluidic microscope 12 is shown in FIG. 2. As shown in FIG. 2, OFM 12 may include an image sensor (or imager) such as image sensor 302 for imaging samples within OFM 12. OFM 12 may include an array of image pixels such as pixel array 304 and image sensor circuitry such as image sensor circuitry 306. Image sensor circuitry 306 may include row control circuitry, column readout circuitry, analog-to-digital conversion circuitry or other circuitry associated with the capture of raw data using image pixel array 304 of imager 302. Circuitry 18 of FIG. 1 may, for example, be used to control imaging functions for OFM 12.

OFM 12 may include optofluidic microscope (OFM) structures such as one more channels through which fluid may flow during operation of OFM 12. Circuitry 18 may be used to operate imager 302 of OFM 12 to capture images of the fluid as it flows through one of the channels of OFM 12. Circuitry 18 may be used to activate flow control components 50 for controlling the flow of fluids in channels of OFM 12. OFM structures 300 may include gates, electrodes, or other components within channels in OFM 12 for controlling the flow of fluids through the channels of OFM 12. Flow control components 50 may include a chemical pump that uses chemical interactions to generate pressure within OFM 12 for controlling the flow of fluids within OFM 12. Flow control components 50 may be used to operate (e.g., toggle or actuate) movable structures of OFM structures 300 during sample analysis operations.

Figure 3:
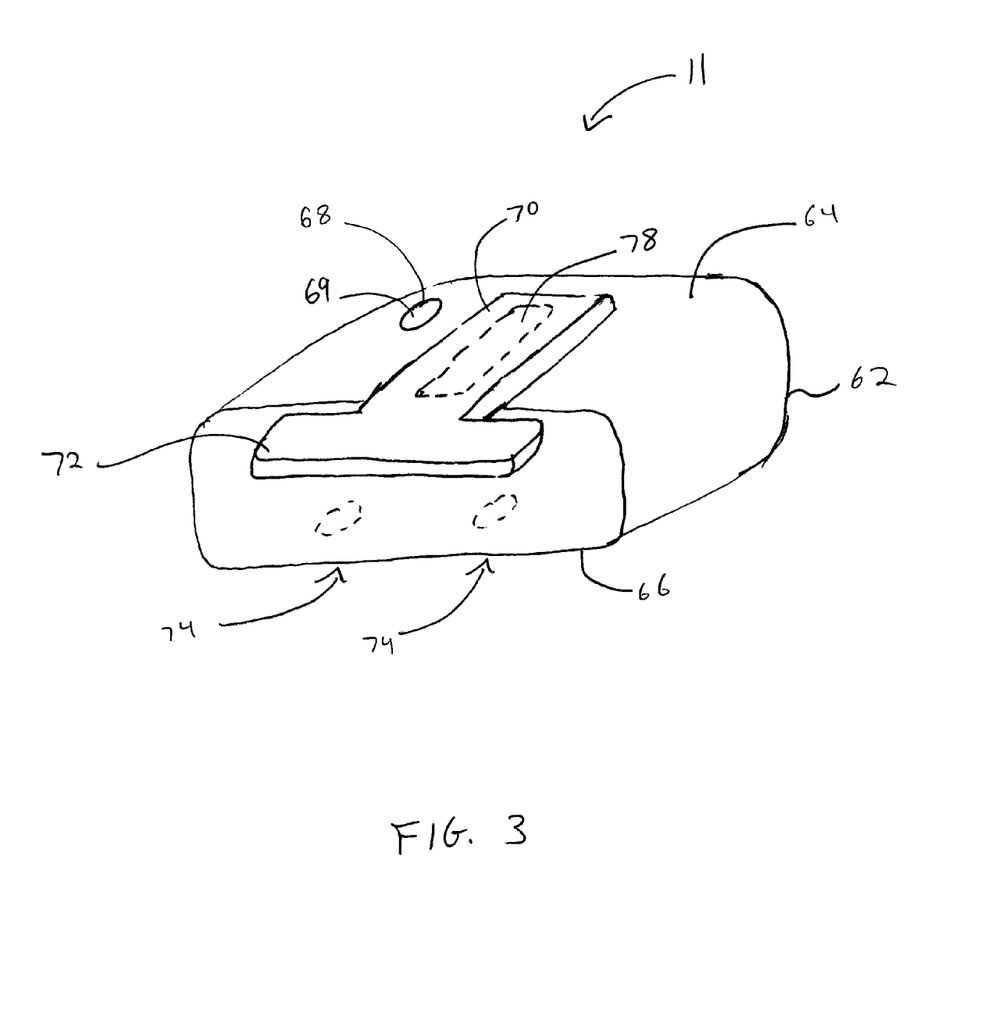
FIG. 3 is a perspective view of an illustrative optofluidic microscope cartridge in accordance with an embodiment of the present invention.

As shown in FIG. 3, OFM cartridge 11 may include a housing 62 having a first surface such as top surface 64 and an opposing second surface such as bottom surface 66. OFM cartridge 11 may include an opening such as sample injection port 68 in a surface such as top surface 64 of housing 62. Sample injection port 68 may be used by a user of system 10 for injecting fluid or other samples into OFM cartridge 11. OFM cartridge 11 may include a protective cover such as removable cover 70 over a transparent portion 78 of housing 62. Removable cover 70 may include an extended portion 72 such as a pull tab for removing removable cover 70. Removing removable cover 70 from OFM cartridge 11 may initiate sample analysis operations. For example, removable cover 70 may be formed, in part, by magnetic materials that, when removed, operate a valve within a chemical pump in OFM cartridge 11 allowing mixing of chemicals. After removable cover 70 has been removed, light may pass through transparent portion 78 of housing 62 into OFM 12 (see FIG. 1) to be used in capturing images of samples that have been injected into sample injection port 68. Sample injection port may include a permeable or semi-permeable cover 69 such as a neoprene membrane through which a needle may be inserted (as an example).

OFM cartridge 11 may include electrical contacts 74 on a surface such as bottom surface 66 of housing 62. Electrical contacts 74 may be coupled to circuitry such as circuitry 18 of OFM cartridge 11. Electrical contacts 74 may be used to couple circuitry 18 of OFM cartridge 11 to circuitry 54 of analysis module 13.

Figure 4:
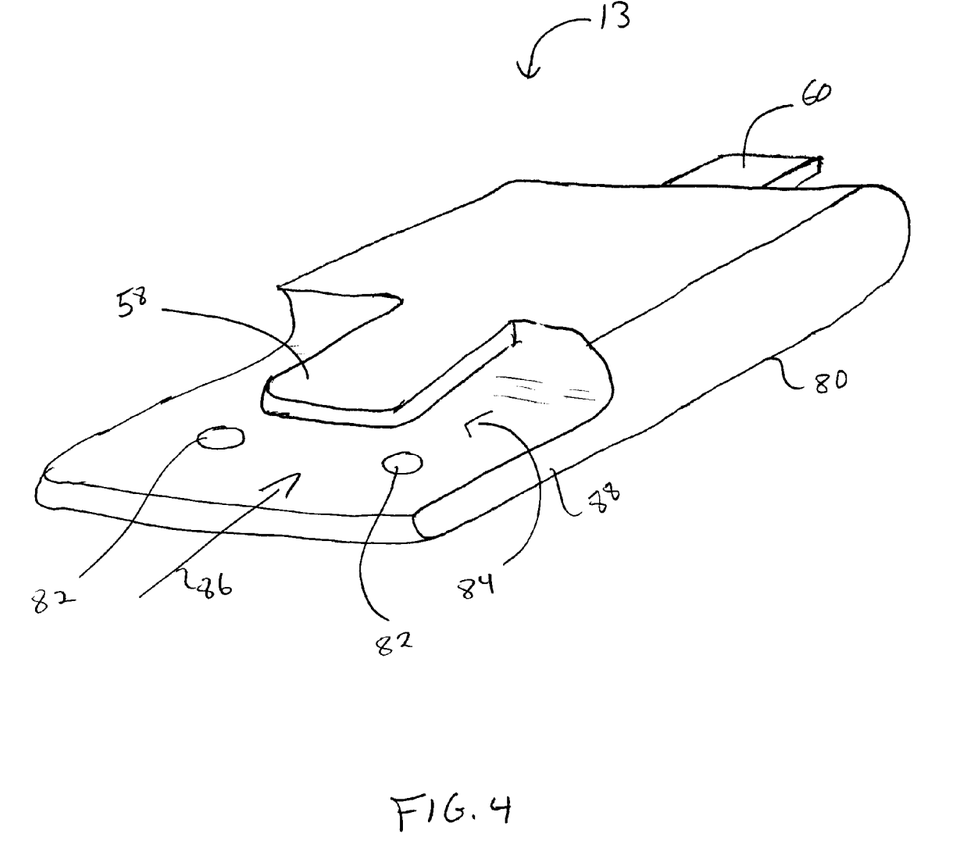
FIG. 4 is a perspective view of an illustrative analysis module for receiving an optofluidic microscope cartridge in accordance with an embodiment of the present invention.

As shown in FIG. 4, analysis module 13 may include a housing such as housing 80. Housing 62 of OFM cartridge 11 may have a shape that corresponds to the shape of housing 80 of analysis module 13 so that housing 62 may be engaged with a protruding portion such as mounting structure 58 of analysis module 13. In the example of FIG. 4, analysis module 80 includes an extended portion 88 that, in combination with mounting structure 58, forms recess 84. OFM cartridge 11 may be coupled with analysis module 13 by inserting OFM cartridge 11 into recess 84 in direction 86. Cover 70 of OFM cartridge 11 may be removed prior to inserting OFM cartridge 11 into recess 84. Portion 88 may include electrical contacts 82. Electrical contacts 82 may be coupled to circuitry 54 within analysis module 13. Electrical contacts 82 may be formed on portion 88 of housing 80 so that contacts 82 couple with contacts 74 of OFM cartridge 11 when OFM cartridge 11 is inserted into recess 84.

As shown in FIG. 4, output port 60 may be implemented as a USB connector for coupling module 13 to external equipment such as a computer, cell phone, laptop computer, tablet computer, etc. Lighting components 52 (see FIG. 1) of analysis module 13 may, for example, be mounted in mounting structure 58 so that light from lighting components 52 passes through transparent portion 78 of OFM cartridge 11 during sample analysis operations.

Figure 5:
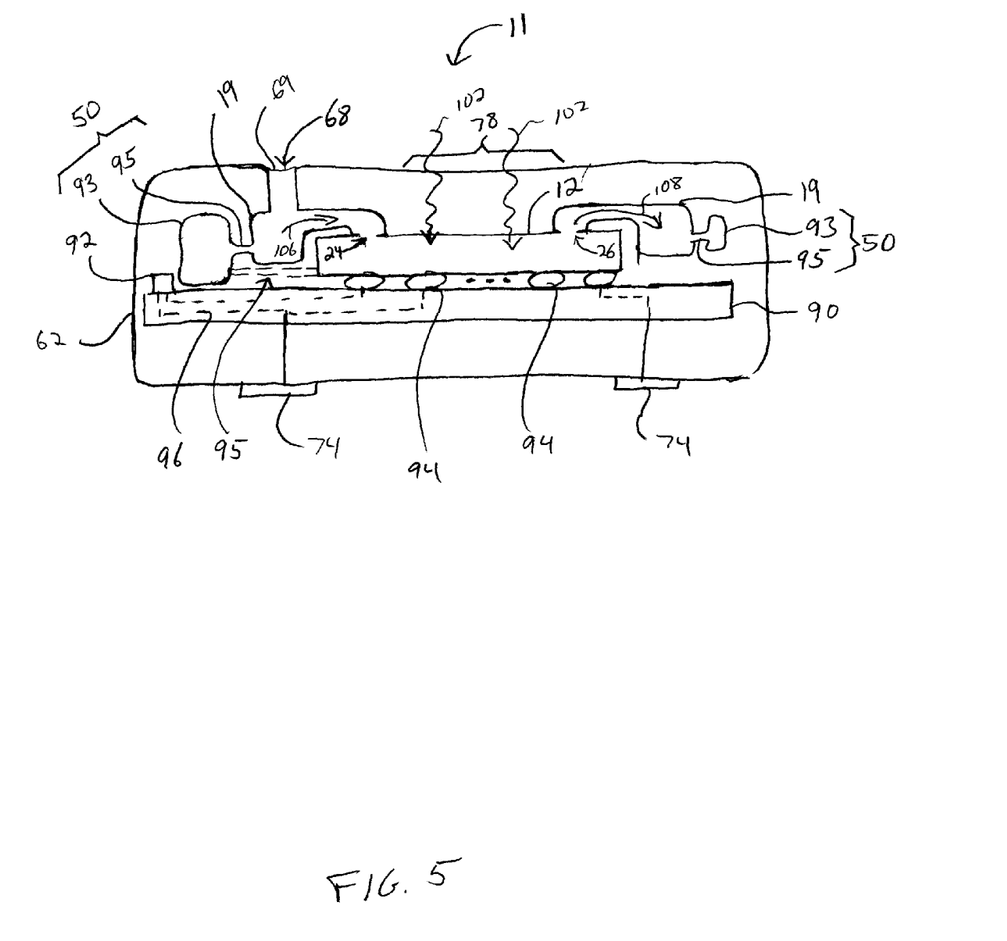
FIG. 5 is a cross-sectional side view of an illustrative optofluidic microscope cartridge in accordance with an embodiment of the present invention.

As shown in the cross-sectional side view of FIG. 5, optofluidic microscope cartridge 11 may include optofluidic microscope 12 coupled to a storage and processing circuitry 18 (see FIG. 1) that is implemented using a printed circuit substrate such as printed circuit board 90, integrated circuits 92 and other circuitry in OFM cartridge 11. OFM 12 may be coupled to printed circuit board 90 using an array of solder balls 94 (e.g., a ball grid array). Printed circuit board 90 may include metal traces 96 for electrically coupling OFM 12 to other circuitry such as integrated circuit 92 or contact pads 74.

OFM cartridge 11 may include one or more sample reservoirs 19. Sample reservoirs 19 may include an input reservoir connected to sample injection port 68 and an output reservoir. Samples injected into input reservoir 19 (e.g., through membrane 69 of port 68) may be moved from reservoir 19 into OFM 12 through opening 24 (as indicated by arrow 106) using flow control components 50. After flowing through OFM 12, samples may be moved into output reservoir 19 through opening 26 (as indicated by arrow 108). Flow control components may include chemically powered pumps such as pumps 93 (sometimes referred to herein as chemical pumps). Chemical pumps 93 may be chemically powered pumps configured to move samples or other fluids within OFM 12 (or into and out of OFM 12) by proving gas pressure to reservoirs 19 (or other portions of OFM 12) through gas lines 95. As shown in FIG. 5, gas lines 95 may include gas lines coupled to reservoirs 19 and/or gas lines coupled directly to OFM 12.

Chemical pumps 93 may be used to provide a constant pressure for moving fluids through OFM 12 while light such as light 102 is passed into OFM 12 through transparent portion 78 of housing 62 of OFM cartridge 11. Light 102 may be used in capturing images of samples as they are moved through OFM 12 using pumps 93. As shown in FIG. 5, OFM cartridge 11 may include one or more pumps coupled to an input reservoir, one or more pumps coupled directly to channels within OFM 12 and/or one or more pumps coupled to an output reservoir (e.g., for reversing the flow of fluids or samples within OFM 12).

Figure 6:
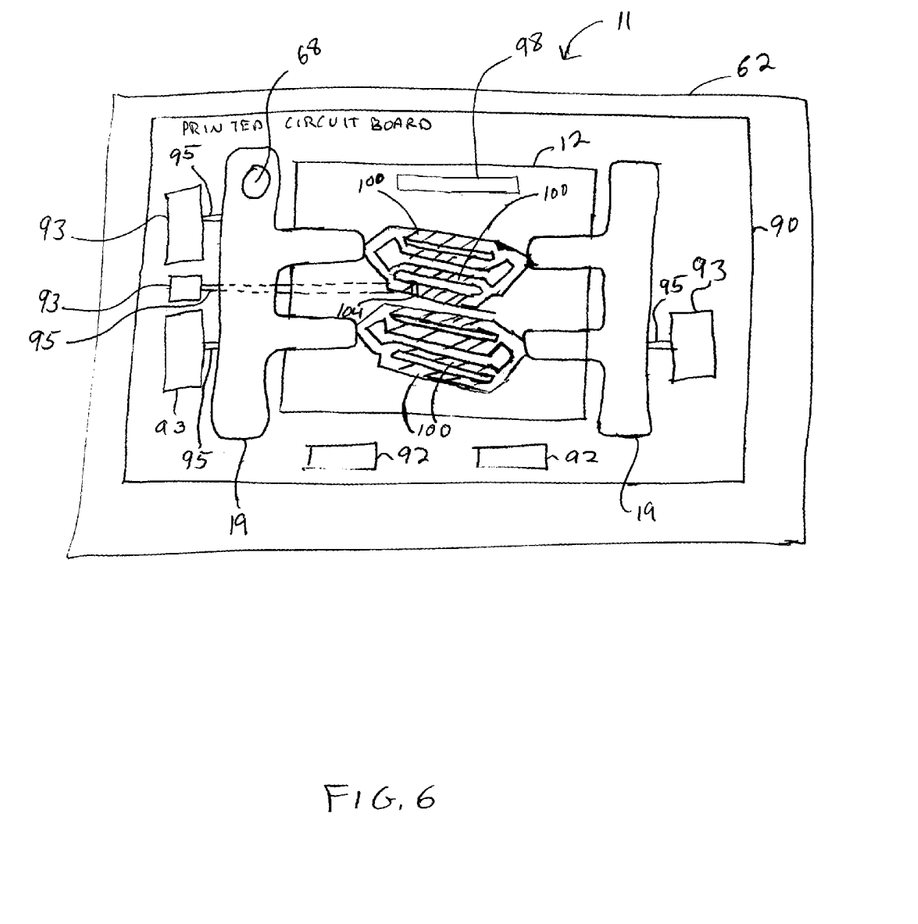
FIG. 6 is a cross-sectional top view of an illustrative optofluidic microscope cartridge in accordance with an embodiment of the present invention.

As shown in the cross-sectional top view of FIG. 6, OFM 12 may include multiple linked channels such as fluid flow channels 100. Chemical pumps 93 may be used to generate gasses that force samples from reservoirs 19 into (and through) channels 100. If desired, channels 100 may include additional flow control components such as gate 104. If desired, one or more pumps 93 may be used to operate a gate such as gate 104 by providing gas pressure to gate 104 through a gas line 95 that is coupled directly to one of fluid flow channels 100. If desired, gate 104 may be operated using pressure that is provided from one of pumps 93 though a gas line 95 that is coupled to gate 104 in any suitable arrangement (e.g., using a gas line that passes through sidewall structures of OFM 12, through entrance ports or exit ports of channels 100 or through portions of an image sensor integrated circuit of OFM 12).

If desired, OFM 12 may be provided with control circuitry such as control circuitry 98 (e.g., an integrated circuit) for operating image sensor circuitry 306 (see FIG. 2). If desired, printed circuit board 90 may include additional circuitry 92 (e.g., one or more integrated circuits mounted to board 90) for operating OFM cartridge 11. Storage and processing circuitry 18 of FIG. 1 may be implemented, in part, using integrated circuits 92 and 98 and printed circuit board 90. Circuitry 92 and circuitry 98 may receive power from an internal power source (e.g., a battery) within OFM cartridge 11 or may receive power externally (e.g., from analysis module 13 through contacts 74).

Figure 7A:
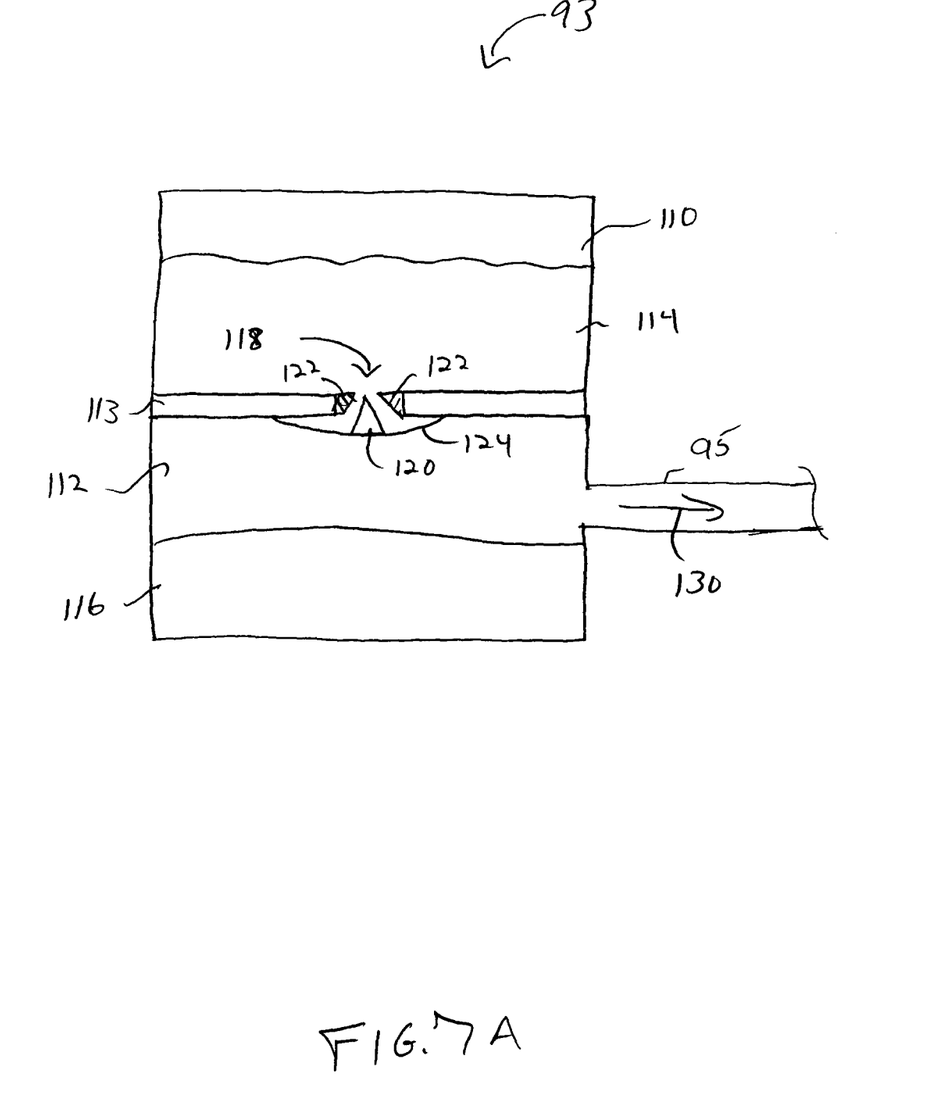
FIG. 7A is a diagram of illustrative chemical pump that may be used to control the flow of fluids in a microfluidic system in accordance with an embodiment of the present invention.

As shown in FIG. 7A, chemical pump 73 may be implemented as a gas generating component having two adjacent chambers 110 and 112. Chamber 110 may contain a first reactant 114 such as liquid reactant (e.g., acetic acid). Chamber 112 may contain a second reactant 116 such as a solid or powder reactant (e.g., sodium bicarbonate). First and second reactants 114 and 116 may be selected to be stable chemicals (e.g., acetic acid (vinegar) and sodium bicarbonate (baking soda) respectively) that, when mixed, generate a gas such as carbon dioxide.

Chambers 110 and 112 may be separated by structural member 113 having an opening such as port 118. Port 118 may be a valve-covered port that is operable to allow fluid reactant 114 into chamber 112 thereby allowing a chemical reaction between reactants 114 and 116 and the release of a significant volume of gas. Port 118 may include a valve member 120 for blocking or regulating the flow of reactant 114 into chamber 112. Valve member 120 may be configured to remain closed prior to activation of OFM cartridge 11 or to subsequently close if the pressure of the generated gas exceeds a specified amount. Valve member 120 may be controlled using a diaphragm 124 or spring-loaded or electrically controlled valve control components 122. Components 122 may, as examples, be springs that are coupled to member 120 or portions of a microsolenoid that generates magnetic fields for actuating valve member 120. For example, components 122 may be formed, in-part, by a microsolenoid that is configured to receive a current that generates a magnetic field within the microsolenoid that exerts a magnetic force on valve member 120.

Valve member 120 can be forced into port 118 to reduce or stop the flow of liquid 114 into the chamber 112, thereby controlling the rate of the reaction between reactants 114 and 116 and thereby controlling the amount of pressure being provided to OFM 12 through gas line 95 (as indicated by arrow 130).

Figure 7B:
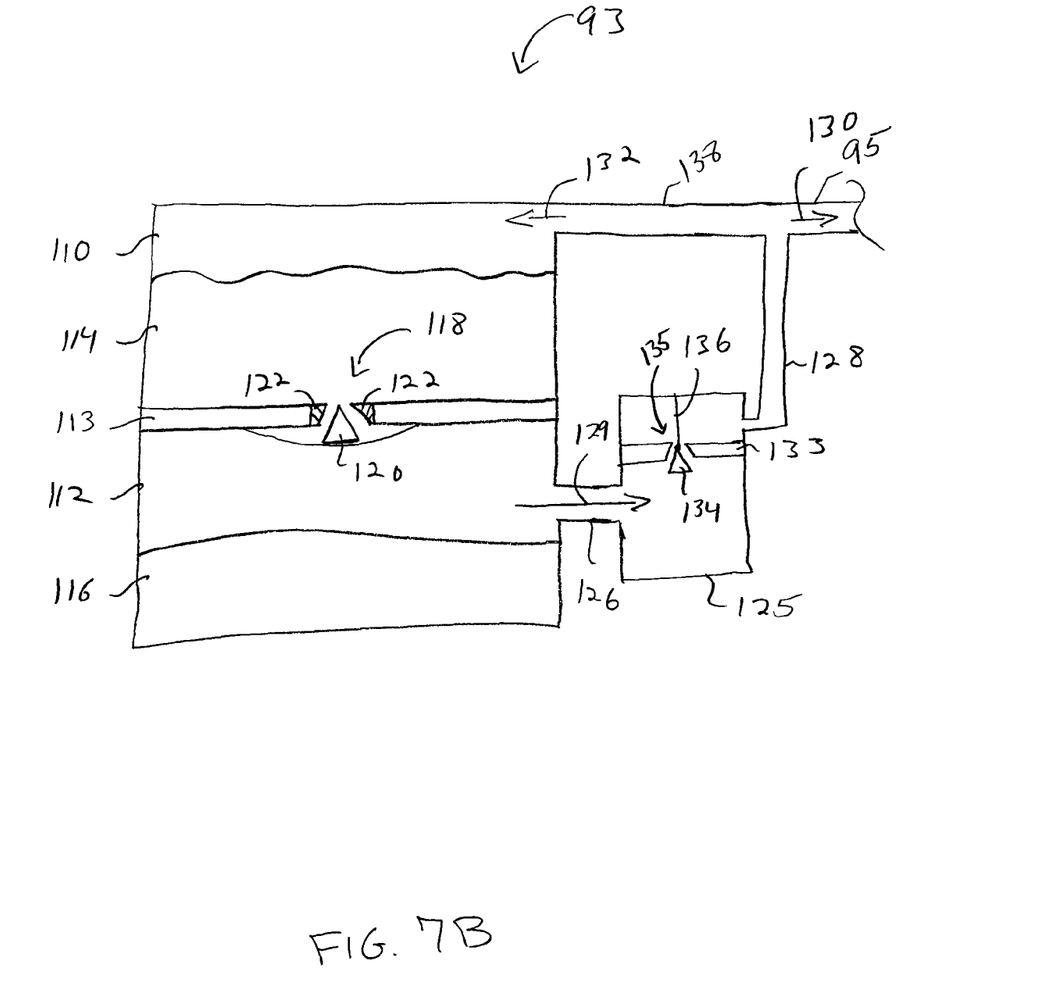
FIG. 7B is a diagram of illustrative chemical pump having a pressure stabilization chamber that may be used to control the flow of fluids in a microfluidic system in accordance with an embodiment of the present invention.

As shown in FIG. 7B, in order to further control the pressure generated by pump 93 and smooth the rate of pressure changes of gasses provided to gas lines such as gas line 95, the gas generated by the chemical reaction between reactants 114 and 116 can pass into an additional chamber such as pressure stabilization chamber 125 through a gas line 126 (as indicated by arrow 129). Stabilization chamber 125 may be split by a structural member 133 that includes pressure regulation valve 135. Pressure regulation valve 135 may include a valve member 134 that is controlled by a pressure sensitive actuator 136 that is configured to close when the pressure of the gas received through line 126 exceeds a certain amount or to otherwise respond to gas pressure such that a relatively constant pressure flow is allowed to pass into gas line 128 and further into the system. As examples, pressure sensitive actuator 136 may be a spring or a diaphragm.

If desired, pressure stabilization chamber 125 may be connected back to the chamber 110 using gas line 138 in order to provide balance pressure in direction 132 to provide a constant pressure in chamber 110 as reactant 114 flows into chamber 112.

Gas generated in pump 93 may be provided through gas line 95 to a microfluidic system such as OFM 12 to provide pressure for moving fluids from one point to another in the system or for operating pressure based valves or gates, thereby controlling the location of fluids within the microfluidic system. In this way, a fully mechanical system can be utilized to control such valves. However, this is merely illustrative. If desired, electrical components such as microsolenoids can be used together with pumps such as pump 93 for managing fluid transfer within the system.

Gases generated by chemical reactions in pump 93 may include gases such as carbon dioxide, nitrogen, and other non-oxidizing or reactive gases can that can in aid processing of biological and chemical samples by preventing unwanted reactions and growths from occurring (as examples).

Initial activation of pump 93 may be accomplished via mechanical, magnetic, electrical and/or other means such that the reactants which have been stored for an indeterminate amount of time in isolation via a closed port 118 are allowed to react when port 118 is opened and intermixing or reactants occurs. As an example of a magnetically controlled valve 118, valve member 120 and removable cover 70 may be formed from magnetic materials. Prior to removal, the location of a magnetic removable cover 70 may, due to its physical location with respect to member 120, apply a magnetic force on member 120 holding member 120 in a closed position. When the cover 70 is removed, the magnetic force may be removed and pressure such as a spring force or diaphragm pressure from components 124 or 122 may force the valve open and allow intermixing of reactants 114 and 116. However, this is merely illustrative, valve member 120 may be actuated to open and close port 118 using any suitable mechanical and/or electrical means.

If desired, multiple chemical pumps 93 connected to a microfluidic system such as OFM 12 may be activated in a desired sequence. For example, pumps 93 may be automatically activated using a valve-opening trigger in one of the two reactant chambers. As an example of a valve-opening trigger, a solid reactant (e.g., reactant 116) may be dissolved to the point that a spring loaded trigger embedded within the solid reactant is freed to move, thereby opening a reactant mixing valve on a subsequent gas generation unit (pump). In this way, OFM cartridge 11 may be provided with the ability to perform extended analysis operations for long term or multiple sample usage.

Figure 8:
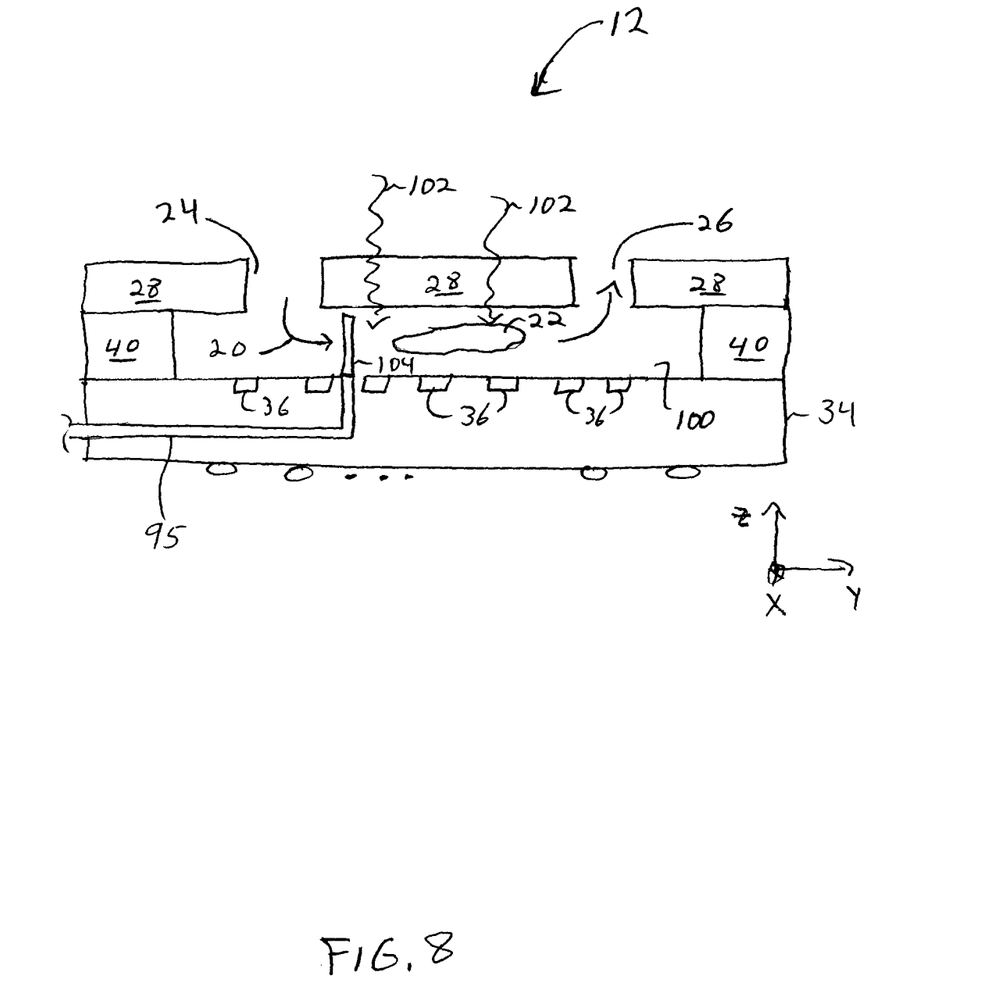
FIG. 8 is a cross-sectional side view of an illustrative optofluidic microscope in accordance with an embodiment of the present invention.

FIG. 8 is a cross-sectional side view of an optofluidic microscope 12 showing how a sample may flow through a fluid flow channel. As shown in FIG. 8, OFM 12 may include an image sensor integrated circuit such as image sensor integrated circuit 34. Image sensor integrated circuit 34 may be formed from a semiconductor substrate material such as silicon and may contain numerous image sensor pixels 36. Image sensor pixels 36 may form part of an array of image sensor pixels on image sensor integrated circuit 34. Some of the pixels may be actively used for gathering light. Other pixels may be inactive or may be omitted from the array during fabrication. In arrays in which fabricated pixels are to remain inactive, the inactive pixels may be covered with metal or other opaque materials, may be depowered, or may otherwise be inactivated. There may be any suitable number of pixels fabricated in integrated circuit 34 (e.g., tens, hundreds, thousands, millions, etc.).

Image sensor integrated circuit 34 may be covered with a transparent layer of material such as glass layer 28 or other clear covering layers. Structures such as standoffs 40 (e.g., polymer standoffs) may be used to elevate the lower surface of glass layer 28 from the upper surface of image sensor integrated circuit 34. This forms one or more channels such as channels 100. Channels 100 may have lateral dimensions (dimensions parallel to dimensions x and z in the example of FIG. 8) of a millimeter or less (as an example). The length of each channel (the dimension of channel 100 along dimension y in the example of FIG. 8) may be 1-10 mm, less than 10 mm, more than 10 mm, or other suitable length. Standoff structures 40 may be patterned to form sidewalls for channels such as channel 100.

During operation, fluid flows through channel 100 as illustrated by arrows 20. Fluid may be introduced into channel 100 through entrance port 24 using pressure generated by pumps such as chemical pumps 93 (see, e.g., FIG. 5). Fluid may exit channel 100 through exit port 26 and may, if desired, be collected in one of reservoirs 19 (see, e.g., FIG. 5). Reservoirs may also be formed within portions of channel 100.

The rate at which fluid flows through channel 16 may be controlled using fluid flow control structures 50. Fluid flow rate control structures 50 that may be used in system 10 may include pumps 93, gates 104, electrodes, microelectromechanical systems (MEMS) devices, etc. Gate 104 in channel 100 may be operated using MEMS devices or using gas pressure provided though a gas line 95 from one of pumps 93. In the example of FIG. 8, a gas lines 95 that is coupled to gate 104 is formed, in part, by a channel within image sensor integrated circuit 34. However, this is merely illustrative. Gas pressure from pumps 93 may be provided to gate 104 using a gas line that passes through structures 40, through structure 28, or through openings 24 or 26 (as examples).

Fluids in channel 100 may contain cells such as cell 22 or other biological elements or particles. As cells such as cells 22 pass by sensor pixels 36, image data may be acquired. In effect, the cell is "scanned" across the pattern of sensor pixels 36 in channel 100 in much the same way that a printed image is scanned in a fax machine. Because the size of each image sensor pixel 36 is typically small (e.g., on the order of 0.5-3 microns or less in width), precise image data may be acquired. This allows high-resolution images of cells such as cell 22 to be produced. A typical cell may have dimensions on the order of 1-10 microns (as an example). Images of other samples (e.g., other biological specimens) may also be acquired in this way. Arrangements in which cells are imaged are sometimes described herein as an example.

Figure 9:
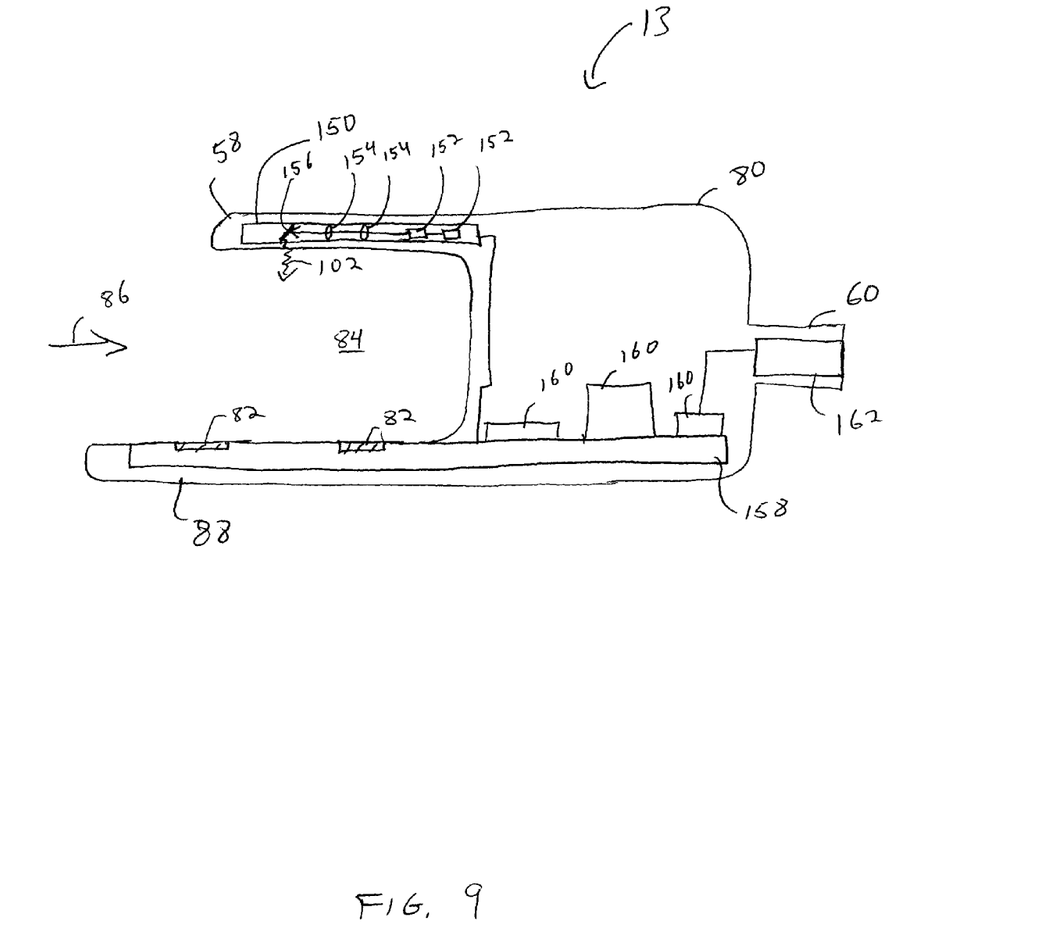
FIG. 9 is a cross-sectional side view of an illustrative analysis module for receiving an optofluidic microscope cartridge in accordance with an embodiment of the present invention.

As shown in FIG. 9, lighting components 52 (FIG. 1) may be implemented as a light source such as light source 150 of analysis module 13 to be used to provide light 102 to OFM 12 during sample imaging operations. As described above in connection with FIG. 4, OFM cartridge 11 may be inserted into recess 84 in housing 80 of analysis module 13 (in direction 86). During sample imaging operations, storage and processing circuitry 54 (see FIG. 1) that is implemented using circuitry such as printed circuit board 158, integrated circuits 160 and other circuitry in analysis module 13 may be used to control the operation of light source 150.

Light source 150 may include one or more light generating components 152, one or more lenses 154 and one or more mirrors 156. Light generating components 152 may include light generating components such as lamps, light-emitting diodes, lasers, or other sources of light. Light source 150 may be a white light source or may contain one or more light-generating elements 152 that emit different colors of light. For example, light-source 150 may contain multiple light-emitting diodes of different colors or may contain white-light light-emitting diodes or other white light sources that are provided with different respective colored filters. In response to control signals from circuitry 54, light source 150 may produce light 102 of a desired color and intensity. Light 102 may be directed out of analysis module 13 and into OFM cartridge 11. For example, light source 150 may be mounted within mounting structure 58 of analysis module 13 so that light 102 passes through transparent portions of housings 80 and 62 (of analysis module 13 and OFM cartridge 11 respectively) and through glass layer 28 of OFM 12 to illuminate the sample in channel 100 (see FIG. 8).

As shown in FIG. 9, output port 60 may include port circuitry 162 such as universal serial bus (USB) circuitry, serial port circuitry, audio port circuitry, video port circuitry, etc. that is coupled to storage and processing circuitry 54 that is implemented as one or more integrated circuits 160.

Figure 10:
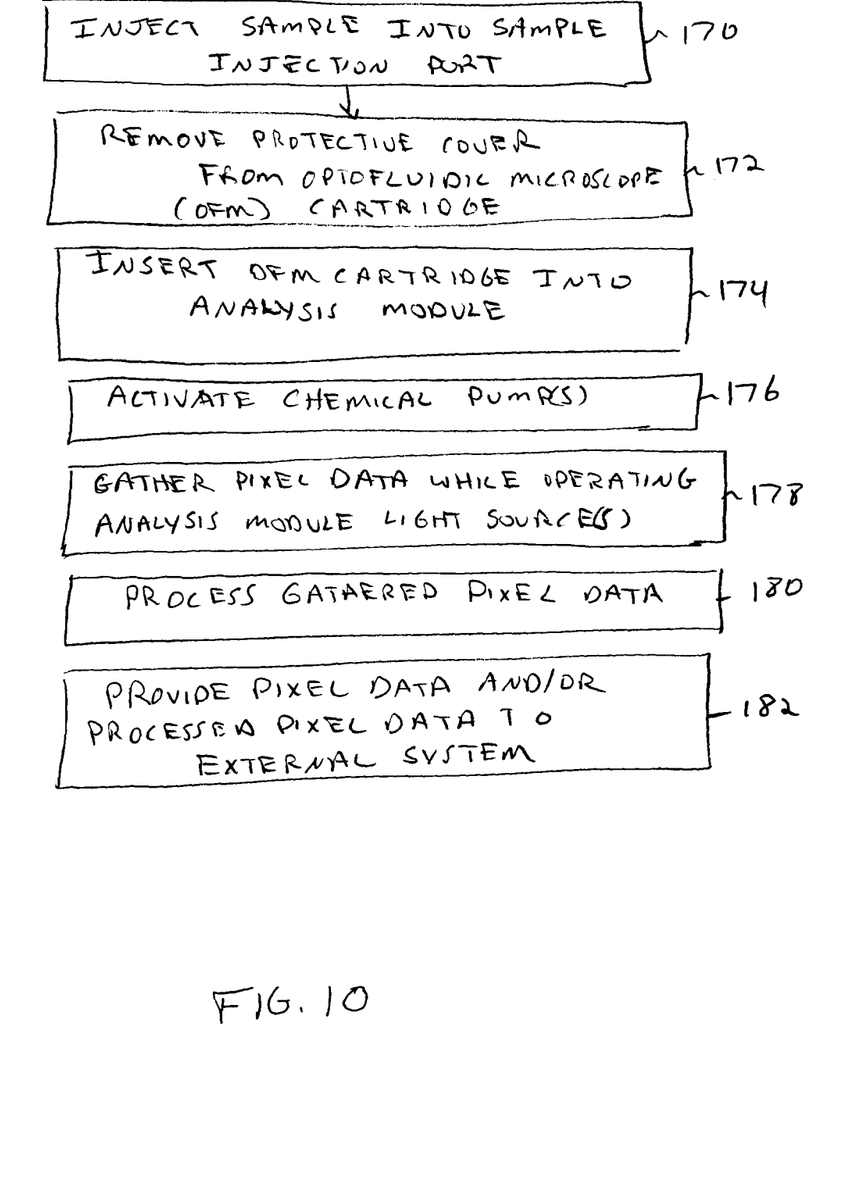
FIG. 10 is a flow chart of illustrative steps that may be used in operating a microfluidic system of the type shown in FIG. 1 in accordance with an embodiment of the present invention.

FIG. 10 is a flow chart of illustrative steps involved in using a system such as system 10 of FIG. 1 in acquiring images of cells or other samples.

At step 170, a sample may be injected into a sample injection port in an optofluidic microscope cartridge in a microfluidic system.

At step 172, a protective cover such as a removable magnetic protective cover may be removed from the optofluidic microscope cartridge.

At step 174, the optofluidic microscope cartridge may be inserted (or otherwise mounted) in an analysis module that is configured to receive the optofluidic microscope cartridge.

At step 176, fluid control components such as chemical pumps in the optofluidic microscope cartridge may be activated. If desired, the chemical pumps may be activated by mechanical or electrical means or may be activated by the act of removing the magnetic protective cover at step 172.

At step 178, an image pixel array in an optofluidic microscope in the optofluidic microscope cartridge may be used to gather pixel data white operating one or more light sources in the analysis module. Operating the light sources in the analysis module may provide light to the optofluidic microscope cartridge to be used in gathering the pixel data.

At step 180, the gathered pixel data may be processed. Processing the gathered pixel data may include extracting sample analysis information from the gathered pixel data, performing image correction operations or other data processing operations. Gathered pixel data may be processed using storage and processing circuitry in the optofluidic microscope cartridge or in the analysis module.

At step 182, the gathered pixel data and/or the processed pixel data may be provided to an external system (e.g., through a USB port or using wireless communications circuitry).

Various embodiments have been described illustrating a microfluidic system for imaging and processing fluids containing cells and other materials. A microfluidic system may include an image sensor integrated circuit containing image sensor pixels. A channel containing a fluid with particles such as cells may be formed on top of the image sensor. Flow control components may be mounted to the image sensor integrated circuit for controlling the location of fluids in the channel.

The flow control components may include a chemically powered pump. The chemical pump may include one or more chambers and a valve between the chambers. The valve may be operable to allow chemical reactants such as acetic acid and sodium bicarbonate that are stored in the chambers to be mixed to produce one or more gasses for generating pressure in the channel. The pressure from the gas in the channel may be used to control the flow of the fluid through the channel. As the fluid and particles flow through the channel, the image sensor pixels may be used to capture images of the particles.

The chemically powered pump may include an additional pressure stabilization chamber having a pressure sensitive valve. The pressure sensitive valve may include a pressure sensitive actuator that is configured to close the valve using a valve member when the pressure of the generated gas exceeds a limit. The chemically powered pump may include one or more gas lines for coupling the pump to other parts of the microfluidic system or to other portions of the pump.

The microfluidic system may include an optofluidic microscope cartridge that is configured to be inserted into a recess in an analysis module. The analysis module and the optofluidic microscope cartridge may each include electrical contacts on an outer surface for electrically coupling the optofluidic microscope cartridge to the analysis module. The analysis module may include a light source that is configured to transmit light through a transparent portion of a housing for the analysis module and through a transparent portion of the surface of the optofluidic microscope cartridge into to the fluid channel in the optofluidic microscope.

The foregoing is merely illustrative of the principles of this invention which can be practiced in other embodiments.

What is claimed is:

1. A microfluidic system, comprising:
   an image sensor integrated circuit containing an array of image sensor pixels;
   a fluid channel on the image sensor integrated circuit that is configured to receive fluid; and
   a pump configured to generate pressure that moves the fluid through the channel by mixing a first chemical reactant with a second chemical reactant in the pump.

2. The microfluidic system defined in claim 1 wherein the pump comprises:
   a first chamber that contains the first chemical reactant; and
   a second chamber that contains the second chemical reactant.

3. The microfluidic system defined in claim 2 wherein the pump further comprises:
   a structural member that separates the first chamber from the second chamber, wherein the structural member has an opening; and
   a valve-covered port in the opening that is operable to allow the first reactant to move from the first chamber into the second chamber.

4. The microfluidic system defined in claim 3 wherein the valve-covered port comprises:
   a movable valve member; and
   a component configured to actuate the movable valve member within the opening.

5. The microfluidic system defined in claim 4 wherein the component comprises a diaphragm configured to exert a force on the movable valve member.

6. The microfluidic system defined in claim 4 wherein the component comprises a spring that is coupled to the moveable valve member.

7. The microfluidic system defined in claim 4 wherein the component comprises a microsolenoid, wherein the movable valve member comprises magnetic material and wherein the microsolenoid is configured to receive a current that exerts a magnetic force on the movable valve member.

8. The microfluidic system defined in claim 3, further comprising:
   a housing; and
   a sample injection port in the housing for allowing the fluid to be injected into the channel.

9. The microfluidic system defined in claim 8, further comprising a removable protective cover mounted to the housing.

10. The microfluidic system defined in claim 9, wherein the movable valve member comprises magnetic material, wherein the removable protective cover comprises magnetic material, and wherein the removable magnetic cover is configured to exert a magnetic force on the movable valve member that holds the movable valve member in a position that prevents the first reactant from moving from the first chamber into the second chamber.

11. The microfluidic system defined in claim 3, further comprising an additional chamber coupled to the second chamber by a gas line, wherein the additional chamber is configured to receive gas that is generated in the second chamber.

12. The microfluidic system defined in claim 11 wherein the additional chamber comprises:
   a structural member that separates a first portion of the additional chamber from a second portion of the additional chamber; and
   a pressure regulation valve in an opening in the structural member that separates the first portion of the additional chamber from the second portion of the additional chamber.

13. The microfluidic system defined in claim 12 wherein the pressure regulation valve comprises:
   a valve member; and
   a pressure sensitive actuator that is configured to close the valve using the valve member when the pressure of the gas that is received from the second chamber exceeds a limit.

14. The microfluidic system defined in claim 13, further comprising first and second additional gas lines, wherein the first additional gas line is coupled between the first portion of the additional chamber and the first chamber, wherein the gas line is coupled between the second portion of the additional chamber and the second chamber, and wherein second additional gas line is coupled between the additional chamber and the fluid channel.

* * * * *